(12) United States Patent
Lorenzo

(10) Patent No.: US 11,871,931 B2
(45) Date of Patent: Jan. 16, 2024

(54) EMBOLIC COIL DELIVERY SYSTEM WITH RETRACTABLE MECHANICAL RELEASE MECHANISM

(71) Applicant: DePuy Synthes Products, Inc., Raynham, MA (US)

(72) Inventor: Juan Lorenzo, Davie, FL (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 324 days.

(21) Appl. No.: 17/065,612

(22) Filed: Oct. 8, 2020

(65) Prior Publication Data

US 2021/0022748 A1 Jan. 28, 2021

Related U.S. Application Data

(60) Continuation of application No. 15/891,041, filed on Feb. 7, 2018, now Pat. No. 10,799,243, which is a
(Continued)

(51) Int. Cl.
*A61B 17/12* (2006.01)
*A61B 17/00* (2006.01)

(52) U.S. Cl.
CPC .... *A61B 17/12109* (2013.01); *A61B 17/1214* (2013.01); *A61B 17/12022* (2013.01);
(Continued)

(58) Field of Classification Search
CPC ........ A61B 17/12109; A61B 17/12022; A61B 17/1214; A61B 17/12154;
(Continued)

(56) References Cited

U.S. PATENT DOCUMENTS 3,429,408 A 2/1969 Maker et al.
5,108,407 A 4/1992 Geremia et al.
(Continued)

FOREIGN PATENT DOCUMENTS

EP 1985244 A2 10/2008
EP 2498691 9/2012
(Continued)

OTHER PUBLICATIONS

Extended European Search Report dated Nov. 18, 2020 in European Patent Application No. 20178690.
(Continued)

*Primary Examiner* — Ashley L Fishback
*Assistant Examiner* — Chima U Igboko
(74) *Attorney, Agent, or Firm* — TROUTMAN PEPPER HAMILTON SANDERS LLP

(57) ABSTRACT

An embolic implantation system configured to deliver an embolic implant intravascularly to a treatment site includes an elongated delivery tube to which the embolic implant is detachably attached by a flexible loop extending through a retaining ring or opening on the embolic implant and an elongated detachment member or pull wire extending through the delivery tube and flexible loop. The pull wire has a bump near its distal end that inhibits the pull wire from moving further distally when the bump presses distally against the flexible loop and/or retaining ring. The flexible loop and retaining ring thereby serve as a distal obstruction obstructing distal movement of the bump and thereby distal movement of the pull wire into the implant.

15 Claims, 5 Drawing Sheets

Related U.S. Application Data division of application No. 14/454,773, filed on Aug. 8, 2014, now Pat. No. 9,918,718.

(52) U.S. Cl.
CPC .................. *A61B 17/12154* (2013.01); *A61B 2017/00867* (2013.01); *A61B 2017/12054* (2013.01); *A61B 2017/12081* (2013.01)

(58) Field of Classification Search
CPC ........... A61B 2017/00867; A61B 2017/12054; A61B 2017/12081; A61B 17/12113; A61B 17/12145; A61M 2025/09175
See application file for complete search history.

(56) References Cited

U.S. PATENT DOCUMENTS

| | | |
|---|---|---|
| 5,122,136 A | 6/1992 | Guglielmi et al. |
| 5,234,437 A | 8/1993 | Sepetka |
| 5,250,071 A | 10/1993 | Palermo |
| 5,263,964 A | 11/1993 | Purdy |
| 5,334,210 A | 8/1994 | Gianturco |
| 5,350,397 A | 9/1994 | Palermo et al. |
| 5,382,259 A | 1/1995 | Phelps et al. |
| 5,392,791 A | 2/1995 | Nyman |
| 5,484,409 A | 1/1996 | Atkinson et al. |
| 5,569,221 A | 10/1996 | Houser et al. |
| 5,899,935 A | 5/1999 | Ding |
| 5,925,059 A | 7/1999 | Palermo et al. |
| 6,113,622 A | 9/2000 | Hieshima |
| 6,203,547 B1 | 3/2001 | Nguyen et al. |
| 6,391,037 B1 | 5/2002 | Greenhalgh |
| 6,454,780 B1 | 9/2002 | Wallace |
| 6,506,204 B2 | 1/2003 | Mazzocchi |
| 6,561,988 B1 | 5/2003 | Turturro et al. |
| 7,367,987 B2 | 5/2008 | Balgobin et al. |
| 7,371,251 B2 | 5/2008 | Mitelberg et al. |
| 7,371,252 B2 | 5/2008 | Balgobin et al. |
| 7,377,932 B2 | 5/2008 | Mitelberg et al. |
| 7,384,407 B2 | 6/2008 | Rodriguez et al. |
| 7,708,754 B2 | 5/2010 | Balgobin et al. |
| 7,708,755 B2 | 5/2010 | Davis, III et al. |
| 7,799,052 B2 | 9/2010 | Balgobin et al. |
| 7,811,305 B2 | 10/2010 | Balgobin et al. |
| 7,819,891 B2 | 10/2010 | Balgobin et al. |
| 7,819,892 B2 | 10/2010 | Balgobin et al. |
| 7,901,444 B2 | 3/2011 | Slazas |
| 7,985,238 B2 | 7/2011 | Balgobin et al. |
| 8,062,325 B2 | 11/2011 | Mitelberg et al. |
| 8,333,796 B2 | 12/2012 | Tompkins et al. |
| 8,926,650 B2 | 1/2015 | Que et al. |
| 8,956,381 B2 | 2/2015 | Que et al. |
| 9,155,540 B2 | 10/2015 | Lorenzo |
| 9,232,992 B2 | 1/2016 | Heidner |
| 9,314,326 B2 | 4/2016 | Wallace et al. |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,120 B2 | 5/2017 | Lagodzki et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Peterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 9,918,718 B2 | 3/2018 | Lorenzo |
| 10,149,676 B2 | 12/2018 | Mirigian et al. |
| 10,285,710 B2 | 5/2019 | Lorenzo et al. |
| 10,292,851 B2 | 5/2019 | Gorochow |
| 10,420,563 B2 | 9/2019 | Hebert et al. |
| 10,517,604 B2 | 12/2019 | Bowman et al. |
| 10,668,258 B1 | 6/2020 | Calhoun et al. |
| 10,806,402 B2 | 10/2020 | Cadieu et al. |
| 10,806,461 B2 | 10/2020 | Lorenzo |
| 2001/0049519 A1 | 12/2001 | Holman et al. |
| 2002/0072705 A1 | 6/2002 | Vrba et al. |
| 2002/0165569 A1 | 11/2002 | Ramzipoor et al. |
| 2003/0009208 A1 | 1/2003 | Snyder et al. |
| 2004/0034363 A1 | 2/2004 | Wilson et al. |
| 2004/0059367 A1 | 3/2004 | Davis et al. |
| 2004/0087964 A1 | 5/2004 | Diaz et al. |
| 2006/0025801 A1 | 2/2006 | Lulo et al. |
| 2006/0064151 A1 | 3/2006 | Guterman |
| 2006/0100687 A1 | 5/2006 | Fahey et al. |
| 2006/0116711 A1 | 6/2006 | Elliott et al. |
| 2006/0116714 A1 | 6/2006 | Sepetka et al. |
| 2006/0135986 A1 | 6/2006 | Wallace et al. |
| 2006/0206139 A1 | 9/2006 | Tekulve |
| 2006/0241685 A1 | 10/2006 | Wilson et al. |
| 2006/0247677 A1 | 11/2006 | Cheng et al. |
| 2006/0276824 A1 | 12/2006 | Mitelberg et al. |
| 2006/0276825 A1 | 12/2006 | Mitelberg et al. |
| 2006/0276826 A1 | 12/2006 | Mitelberg et al. |
| 2006/0276827 A1 | 12/2006 | Mitelberg et al. |
| 2006/0276830 A1 | 12/2006 | Balgobin et al. |
| 2006/0276833 A1 | 12/2006 | Balgobin et al. |
| 2007/0010850 A1 | 1/2007 | Balgobin et al. |
| 2007/0055302 A1 | 3/2007 | Henry et al. |
| 2007/0083132 A1 | 4/2007 | Sharrow |
| 2007/0233168 A1 | 10/2007 | Davis et al. |
| 2007/0270903 A1 | 11/2007 | Davis, III et al. |
| 2008/0027561 A1 | 1/2008 | Mitelberg et al. |
| 2008/0045997 A1 | 2/2008 | Balgobin et al. |
| 2008/0097462 A1 | 4/2008 | Mitelberg et al. |
| 2008/0119887 A1 | 5/2008 | Que et al. |
| 2008/0269721 A1 | 10/2008 | Balgobin et al. |
| 2008/0281350 A1 | 11/2008 | Sepetka |
| 2008/0300616 A1 | 12/2008 | Que et al. |

(56) References Cited

U.S. PATENT DOCUMENTS

| | | | |
|---|---|---|---|
| 2008/0306503 A1* | 12/2008 | Que | A61B 17/12022 606/191 |
| 2009/0062726 A1 | 3/2009 | Ford et al. | |
| 2009/0099592 A1 | 4/2009 | Buiser et al. | |
| 2009/0312748 A1 | 12/2009 | Johnson et al. | |
| 2010/0094395 A1 | 4/2010 | Kellett | |
| 2010/0114017 A1 | 5/2010 | Lenker et al. | |
| 2010/0206453 A1 | 8/2010 | Leeflang et al. | |
| 2010/0324649 A1 | 12/2010 | Mattsson | |
| 2011/0092997 A1 | 4/2011 | Kang | |
| 2011/0118776 A1 | 5/2011 | Chen et al. | |
| 2011/0202085 A1 | 8/2011 | Loganathan et al. | |
| 2011/0295303 A1 | 12/2011 | Freudenthal | |
| 2012/0035707 A1 | 2/2012 | Mitelberg et al. | |
| 2012/0041472 A1 | 2/2012 | Tan et al. | |
| 2012/0083868 A1 | 4/2012 | Shrivastava et al. | |
| 2012/0172913 A1 | 7/2012 | Kurrus et al. | |
| 2012/0172921 A1 | 7/2012 | Yamanaka et al. | |
| 2012/0179194 A1 | 7/2012 | Wilson et al. | |
| 2012/0283768 A1 | 11/2012 | Cox et al. | |
| 2012/0289772 A1 | 11/2012 | O'Connell et al. | |
| 2013/0066413 A1 | 3/2013 | Jin et al. | |
| 2013/0296915 A1 | 11/2013 | Bodewadt | |
| 2013/0325054 A1 | 12/2013 | Watson | |
| 2014/0058435 A1 | 2/2014 | Jones et al. | |
| 2014/0135812 A1 | 5/2014 | Divino et al. | |
| 2014/0200607 A1 | 7/2014 | Sepetka et al. | |
| 2014/0243883 A1 | 8/2014 | Tsukashima et al. | |
| 2014/0277084 A1 | 9/2014 | Mirigian et al. | |
| 2014/0277085 A1 | 9/2014 | Mirigian et al. | |
| 2014/0277092 A1 | 9/2014 | Teoh et al. | |
| 2014/0277093 A1 | 9/2014 | Guo et al. | |
| 2014/0277100 A1 | 9/2014 | Kang | |
| 2015/0005808 A1 | 1/2015 | Chouinard et al. | |
| 2015/0025562 A1 | 1/2015 | Dinh et al. | |
| 2015/0182227 A1 | 7/2015 | Le et al. | |
| 2015/0230802 A1 | 8/2015 | Lagodzki et al. | |
| 2015/0335333 A1 | 11/2015 | Jones et al. | |
| 2016/0008003 A1 | 1/2016 | Kleshinski et al. | |
| 2016/0022275 A1 | 1/2016 | Garza | |
| 2016/0022445 A1 | 1/2016 | Ruvalcaba et al. | |
| 2016/0045347 A1 | 2/2016 | Smouse et al. | |
| 2016/0157869 A1 | 6/2016 | Elgård et al. | |
| 2016/0228125 A1 | 8/2016 | Pederson, Jr. et al. | |
| 2016/0278782 A1 | 9/2016 | Anderson et al. | |
| 2016/0310304 A1 | 10/2016 | Mialhe | |
| 2016/0331383 A1 | 11/2016 | Hebert et al. | |
| 2016/0346508 A1 | 12/2016 | Williams et al. | |
| 2017/0007264 A1 | 1/2017 | Cruise et al. | |
| 2017/0007265 A1 | 1/2017 | Guo et al. | |
| 2017/0020670 A1 | 1/2017 | Murray et al. | |
| 2017/0020700 A1 | 1/2017 | Bienvenu et al. | |
| 2017/0027640 A1 | 2/2017 | Kunis et al. | |
| 2017/0027692 A1 | 2/2017 | Bonhoeffer et al. | |
| 2017/0027725 A1 | 2/2017 | Argentine | |
| 2017/0035436 A1 | 2/2017 | Morita | |
| 2017/0035567 A1 | 2/2017 | Duffy | |
| 2017/0042548 A1 | 2/2017 | Lam | |
| 2017/0049596 A1 | 2/2017 | Schabert | |
| 2017/0071737 A1 | 3/2017 | Kelley | |
| 2017/0072452 A1 | 3/2017 | Monetti et al. | |
| 2017/0079671 A1 | 3/2017 | Morero et al. | |
| 2017/0079680 A1 | 3/2017 | Bowman | |
| 2017/0079766 A1 | 3/2017 | Wang et al. | |
| 2017/0079767 A1 | 3/2017 | Leon-Yip | |
| 2017/0079812 A1 | 3/2017 | Lam et al. | |
| 2017/0079817 A1 | 3/2017 | Sepetka et al. | |
| 2017/0079819 A1 | 3/2017 | Pung et al. | |
| 2017/0079820 A1 | 3/2017 | Lam et al. | |
| 2017/0086851 A1 | 3/2017 | Wallace et al. | |
| 2017/0086996 A1 | 3/2017 | Peterson et al. | |
| 2017/0095258 A1 | 4/2017 | Tassoni et al. | |
| 2017/0095259 A1 | 4/2017 | Tompkins et al. | |
| 2017/0100126 A1 | 4/2017 | Bowman et al. | |
| 2017/0100141 A1 | 4/2017 | Morero et al. | |
| 2017/0100143 A1 | 4/2017 | Granfield | |
| 2017/0100183 A1 | 4/2017 | Iaizzo et al. | |
| 2017/0105739 A1 | 4/2017 | Dias et al. | |
| 2017/0113023 A1 | 4/2017 | Steingisser et al. | |
| 2017/0147765 A1 | 5/2017 | Mehta | |
| 2017/0151032 A1 | 6/2017 | Loisel | |
| 2017/0165062 A1 | 6/2017 | Rothstein | |
| 2017/0165065 A1 | 6/2017 | Rothstein et al. | |
| 2017/0165454 A1 | 6/2017 | Tuohy et al. | |
| 2017/0172581 A1 | 6/2017 | Bose et al. | |
| 2017/0172766 A1 | 6/2017 | Vong et al. | |
| 2017/0172772 A1 | 6/2017 | Khenansho | |
| 2017/0189033 A1 | 7/2017 | Sepetka et al. | |
| 2017/0189035 A1 | 7/2017 | Porter | |
| 2017/0215902 A1 | 8/2017 | Leynov et al. | |
| 2017/0216484 A1 | 8/2017 | Cruise et al. | |
| 2017/0224350 A1 | 8/2017 | Shimizu et al. | |
| 2017/0224355 A1 | 8/2017 | Bowman et al. | |
| 2017/0224467 A1 | 8/2017 | Piccagli et al. | |
| 2017/0224511 A1 | 8/2017 | Dwork et al. | |
| 2017/0224953 A1 | 8/2017 | Tran et al. | |
| 2017/0231749 A1 | 8/2017 | Perkins et al. | |
| 2017/0245864 A1 | 8/2017 | Franano et al. | |
| 2017/0245885 A1 | 8/2017 | Lenker | |
| 2017/0252064 A1 | 9/2017 | Staunton | |
| 2017/0258476 A1 | 9/2017 | Hayakawa et al. | |
| 2017/0265983 A1 | 9/2017 | Lam et al. | |
| 2017/0281192 A1 | 10/2017 | Tieu et al. | |
| 2017/0281331 A1 | 10/2017 | Perkins et al. | |
| 2017/0281344 A1 | 10/2017 | Costello | |
| 2017/0281909 A1 | 10/2017 | Northrop et al. | |
| 2017/0281912 A1 | 10/2017 | Melder et al. | |
| 2017/0290593 A1 | 10/2017 | Cruise et al. | |
| 2017/0290654 A1 | 10/2017 | Sethna | |
| 2017/0296324 A1 | 10/2017 | Argentine | |
| 2017/0296325 A1 | 10/2017 | Marrocco et al. | |
| 2017/0303939 A1 | 10/2017 | Greenhalgh et al. | |
| 2017/0303942 A1 | 10/2017 | Greenhalgh et al. | |
| 2017/0303947 A1 | 10/2017 | Greenhalgh et al. | |
| 2017/0303948 A1 | 10/2017 | Wallace et al. | |
| 2017/0304041 A1 | 10/2017 | Argentine | |
| 2017/0304097 A1 | 10/2017 | Corwin et al. | |
| 2017/0304595 A1 | 10/2017 | Nagasrinivasa et al. | |
| 2017/0312109 A1 | 11/2017 | Le | |
| 2017/0312484 A1 | 11/2017 | Shipley et al. | |
| 2017/0316561 A1 | 11/2017 | Helm et al. | |
| 2017/0319826 A1 | 11/2017 | Bowman et al. | |
| 2017/0333228 A1 | 11/2017 | Orth et al. | |
| 2017/0333236 A1 | 11/2017 | Greenan | |
| 2017/0333678 A1 | 11/2017 | Bowman et al. | |
| 2017/0340383 A1 | 11/2017 | Bloom et al. | |
| 2017/0348014 A1 | 12/2017 | Wallace et al. | |
| 2017/0348514 A1 | 12/2017 | Guyon et al. | |
| 2017/0367712 A1 | 12/2017 | Johnson et al. | |
| 2018/0028779 A1 | 2/2018 | von Oepen et al. | |
| 2018/0036508 A1 | 2/2018 | Ozasa et al. | |
| 2018/0078263 A1 | 3/2018 | Stoppenhagen et al. | |
| 2018/0228493 A1 | 8/2018 | Aguilar et al. | |
| 2018/0250150 A1 | 9/2018 | Majercak et al. | |
| 2018/0280667 A1 | 10/2018 | Keren | |
| 2018/0289375 A1 | 10/2018 | Hebert et al. | |
| 2018/0296222 A1 | 10/2018 | Hebert et al. | |
| 2018/0325706 A1 | 11/2018 | Hebert et al. | |
| 2019/0142565 A1 | 5/2019 | Follmer et al. | |
| 2019/0159784 A1 | 5/2019 | Sananes et al. | |
| 2019/0192162 A1 | 6/2019 | Lorenzo et al. | |
| 2019/0231566 A1 | 8/2019 | Tassoni et al. | |
| 2019/0255290 A1 | 8/2019 | Snyder et al. | |
| 2019/0314033 A1 | 10/2019 | Mirigian et al. | |
| 2019/0328398 A1 | 10/2019 | Lorenzo | |
| 2020/0138448 A1 | 5/2020 | Dasnurkar et al. | |
| 2020/0147347 A1 | 5/2020 | Cottone | |
| 2020/0187951 A1 | 6/2020 | Blumenstyk | |
| 2020/0229957 A1 | 7/2020 | Bardsley et al. | |
| 2020/0397444 A1 | 12/2020 | Montidoro et al. | |
| 2021/0001082 A1 | 1/2021 | Lorenzo et al. | |
| 2021/0045759 A1 | 2/2021 | Mehri et al. | |
| 2021/0085498 A1 | 3/2021 | Nygaard et al. | |

(56) References Cited

U.S. PATENT DOCUMENTS

| | | |
|---|---|---|
| 2021/0186513 A1 | 6/2021 | Hoshino et al. |
| 2021/0196281 A1 | 7/2021 | Blumenstyk et al. |
| 2021/0353299 A1 | 11/2021 | Hamel et al. |

FOREIGN PATENT DOCUMENTS

| | | |
|---|---|---|
| EP | 2014-399 A | 1/2014 |
| EP | 3092956 A1 | 11/2016 |
| EP | 3501427 A1 | 6/2019 |
| EP | 3799803 A1 | 4/2021 |
| EP | 3854321 A1 | 7/2021 |
| EP | 1188414 A1 | 3/2022 |
| EP | 4119065 A1 | 1/2023 |
| JP | 2006-334408 A | 12/2006 |
| JP | 2012-523943 A | 10/2012 |
| JP | 2013-78584 A | 5/2013 |
| WO | WO 2008/064209 A1 | 5/2008 |
| WO | WO 2009/132045 A2 | 10/2009 |
| WO | WO 2012/158152 A1 | 11/2012 |
| WO | WO 2016/014985 A1 | 1/2016 |
| WO | WO 2017/066386 A1 | 4/2017 |
| WO | WO 2018/022186 A1 | 2/2018 |
| WO | WO 2020/148768 A1 | 7/2020 |

OTHER PUBLICATIONS

Extended European Search Report dated Dec. 18, 2020 in European Patent Application No. 20181340.

Notification of Reasons for Refusal issued in corresponding Japanese Patent Application No. 2015-156969 dated May 5, 2019 (English translation only).

European Search Report dated Dec. 16, 2015, issued in corresponding Application No. 15180230.3-1654.

* cited by examiner

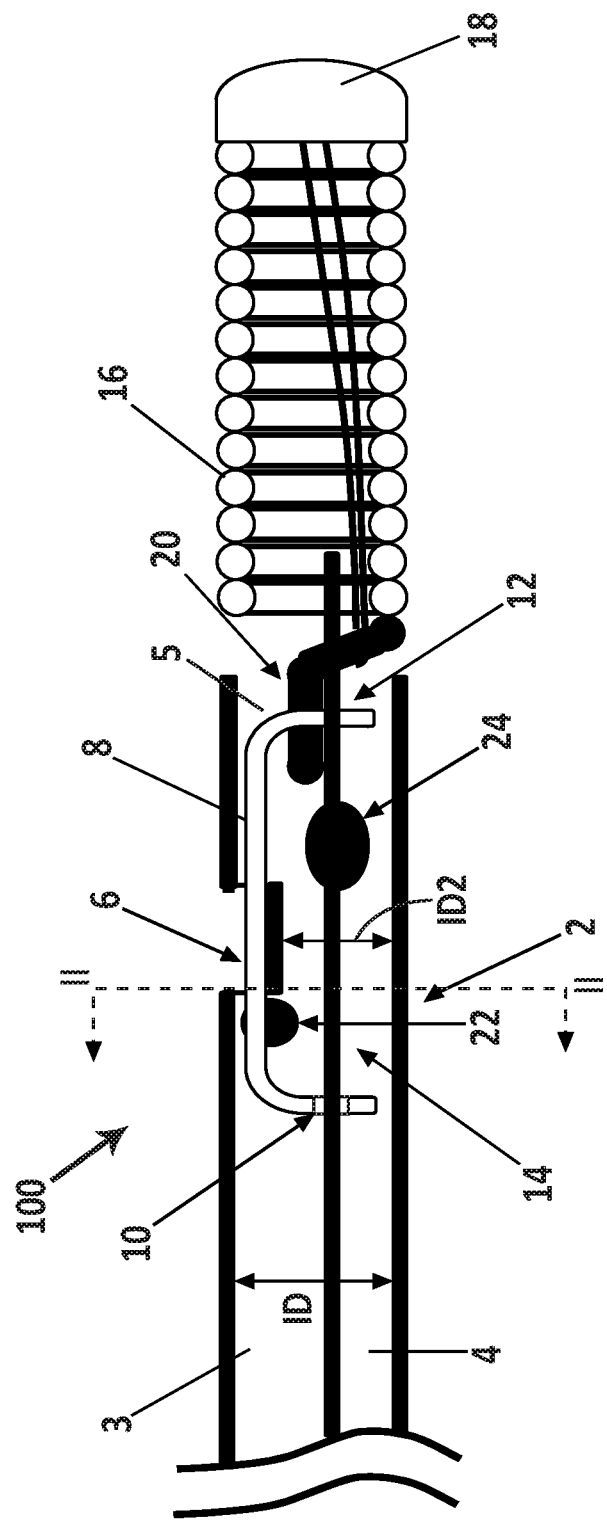
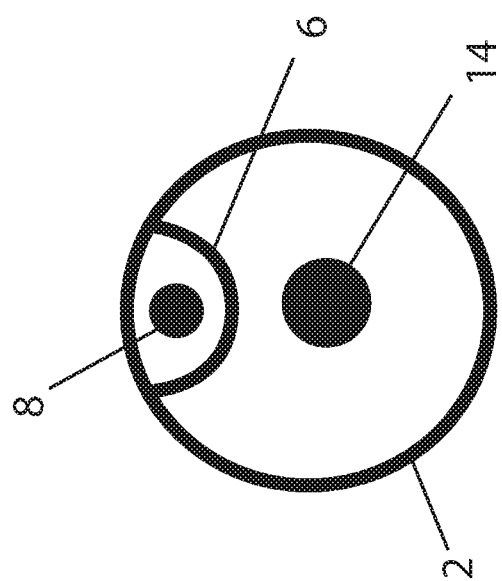
Fig. 1
Fig. 2

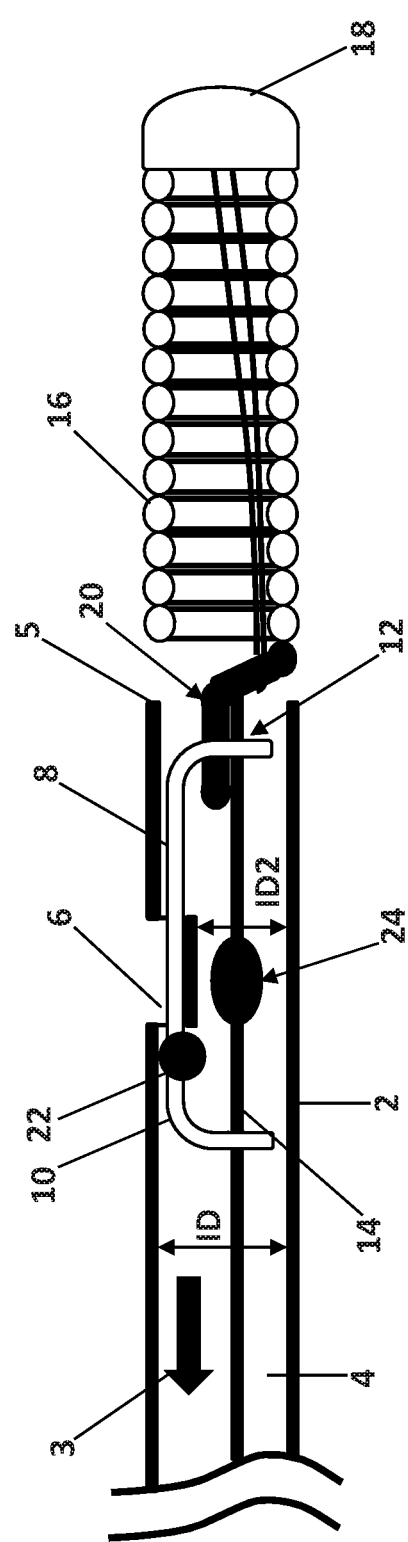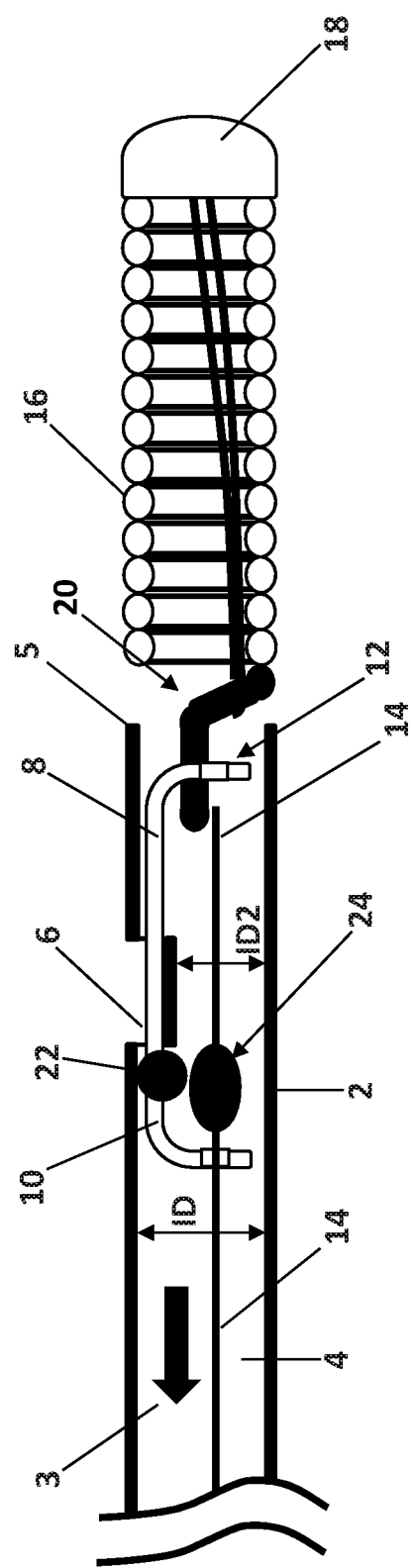

EMBOLIC COIL DELIVERY SYSTEM WITH RETRACTABLE MECHANICAL RELEASE MECHANISM

CROSS-REFERENCE TO RELATED APPLICATIONS

This application is a Continuation of U.S. application Ser. No. 15/891,041, filed Feb. 7, 2018 which is a Divisional of U.S. application Ser. No. 14/454,773, filed Aug. 8, 2014 and issued as U.S. Pat. No. 9,918,718 on Mar. 20, 2018. Each of the parent applications are respectively incorporated herein by reference in their entirety.

FIELD OF THE INVENTION

The present invention relates to a medical device for placing an embolic device at a predetermined site within a vessel of the human body, and more particularly, relates to a catheter-based deployment system for delivering an embolic device.

BACKGROUND

For many years, flexible catheters have been used to place various devices within the vessels of the human body. Such devices include dilation balloons, radiopaque fluids, liquid medications, and various types of occlusion devices such as balloons and embolic coils. Examples of such catheter-based devices are disclosed in U.S. Pat. No. 5,108,407, entitled "Method and Apparatus for Placement of an Embolic Coil" and U.S. Pat. No. 5,122,136, entitled "Endovascular Electrolytically Detachable Guidewire Tip For The Electroformation Of Thrombus In Arteries, Veins, Aneurysms, Vascular Malformations And Arteriovenous Fistulas." These patents disclose catheter-based devices for delivering embolic coils to preselected positions within vessels of the human body in order to treat aneurysms, or alternatively, to occlude blood vessels at a particular location.

Coils which are placed in vessels may take the form of helically wound coils, or alternatively, may take the form of randomly wound coils, coils wound within coils or other such coil configurations. Examples of various coil configurations are disclosed in U.S. Pat. No. 5,334,210, entitled "Vascular Occlusion Assembly" and U.S. Pat. No. 5,382,259, entitled "Vasoocclusion Coil with Attached Tubular Woven or Braided Fibrous Covering." Embolic coils are generally formed of a radiopaque metallic material, such as platinum, gold, tungsten, or alloys of these metals. Often, several coils are placed at a given location to occlude the flow of blood through the vessel, or aneurysm, by promoting thrombus formation at the particular site.

In the past, embolic coils have been placed within the distal end of a catheter. When the distal end of the catheter is properly positioned, the coil may then be pushed out of the end of the catheter with a pusher member to release the coil at the desired location. This procedure for placement of an embolic coil is conducted under fluoroscopic visualization such that the movement of the coil through the vasculature of the body may be monitored and the coil placed at the desired location.

Another procedure involves the use of glue or solder for attaching the coil to a guidewire, which in turn, is placed within a flexible catheter for positioning the coil within the vessel at a preselected position. Once the coil is in the desired position, the coil is held in position by the catheter and the guidewire is pulled proximally to thereby cause the coil to become detached from the guidewire and released from the catheter. Such a coil positioning system is disclosed in U.S. Pat. No. 5,263,964 entitled "Coaxial Traction Detachment Apparatus and Method."

Still another coil positioning procedure is that of having a catheter with a socket at the distal end of the catheter for retaining a ball which is, in turn, bonded to the proximal end of the coil. The ball, which is generally larger in diameter than the outside diameter of the coil, is placed in the socket within the lumen at the distal end of the catheter and the catheter is then moved into a vessel in order to place the coil at a desired position. Once the position is reached, a pusher wire with a piston at the end thereof is pushed distally from the proximal end of the catheter to push the ball out of the socket in order to release the coil at the desired position. Such a system is disclosed in U.S. Pat. No. 5,350,397, entitled "Axially Detachable Embolic Coil Assembly."

Another procedure for placing an embolic coil within a vessel is that of using a heat releasable adhesive bond for retaining the coil at the distal end of the catheter. One such system uses laser energy transmitted through a fiber optic cable to apply heat to the adhesive bond in order to release the coil from the end of the catheter. Such a procedure is disclosed in U.S. Pat. No. 5,108,407 entitled "Method and Apparatus for Placement of an Embolic Coil."

Yet another coil deployment system incorporates a catheter having a lumen throughout the length of the catheter and a distal tip for retaining the coil for positioning the coil at a preselected site. The distal tip of the catheter is formed of a material which exhibits the characteristic that when the lumen of the catheter is pressurized the distal tip expands radially to release the coil at the preselected site. Such a deployment system is disclosed in U.S. Pat. No. 6,113,622 entitled "Embolic Coil Hydraulic Deployment System."

Still another coil deployment system incorporates an interlocking mechanism on the coil. The interlocking end on the embolic coil couples with a similar interlocking mechanism on a pusher assembly. A control wire which extends through the locking mechanism secures the coil to the pusher assembly. The pusher assembly and embolic coil are initially disposed within the lumen of a catheter. When the embolic coil is pushed out of the end of the catheter for placement, the control wire is retracted, and the coil disengages from the pusher assembly. Such a deployment system is disclosed in U.S. Pat. No. 5,925,059, entitled "Detachable Embolic Coil Assembly."

Yet another coil deployment system incorporates an embolic device detachably mounted on the distal portion of a pusher member and held in place with a connector thread or fiber. The fiber passes through a cutter member that may be activated to cut the connector fiber. Once the connector fiber is cut, the embolic device is released. Such a deployment system is disclosed in Published U.S. Patent Application No. 2002/0165569, entitled "Intravascular Device Deployment Mechanism Incorporating Mechanical Detachment."

Still another coil deployment system incorporates an embolic device with a stretch resistant member there through. The distal end of the stretch resistant member attaches to the embolic coil and the proximal end of the stretch resistant member is detachably mounted on the pusher member through various means such as adhesive, or by a connector fiber adhered to or tied to the pusher member, and is detachable by the application of heat. Such a deployment system is disclosed in Published U.S. Patent Application No. 2004/0034363, entitled "Stretch Resistant Therapeutic Device."

A yet further coil deployment system incorporates a pusher wire with a stiff wavy-shaped end segment which is coupled to the embolic coil and is placed in the lumen of the catheter. The coil is advanced through the catheter until it reaches a predetermined site in the vessel at which time the pusher wire is retracted and the embolic coil is released. Such a system is disclosed in U.S. Pat. No. 6,203,547, entitled "Vaso-occlusion Apparatus Having A Manipulable Mechanical Detachment Joint And A Method For Using The Apparatus."

A still further embolic device deployment system for placement of an embolic device, or coil, includes a delivery catheter and a flexible pusher member. The embolic device is retained by an interlocking mechanism which includes a detachment member which extends through an aperture in an engagement member. The engagement member engages a ring on the embolic device. When the detachment member is withdrawn from the aperture, the embolic device is released. One such deployment system is disclosed in U.S. Pat. No. 7,377,932, entitled "Embolic Coil Delivery System with Mechanical Release Mechanism."

A yet still further embolic device deployment system for placement of a stretch-resistant embolic device, or coil, includes a delivery catheter and a flexible pusher member. The embolic device is retained by an interlocking mechanism with a detachment member which extends through an aperture in an engagement member. The engagement member enables a ring on the embolic device, where a stretch-resistant member extends through the coil. When the detachment member is withdrawn from the aperture, the stretch-resistant member enables the embolic device to release without difficulty. One such deployment system is disclosed in U.S. Pat. No. 7,371,251 entitled "Stretch Resistant Embolic Coil Delivery System With Mechanical Release Mechanism."

However, all of the above systems have their drawbacks, including some difficulty in positively and smoothly releasing the embolic coil. Thus, a system is still needed to accomplish these goals.

SUMMARY

Thus, an example of an embolic device deployment system to place an embolic device at a predetermined site within a vessel can include an elongated flexible deployment catheter having a first lumen extending therethrough and having proximal and distal ends. A notch section can be disposed in the first lumen of the catheter and can form a second lumen. An embolic device can have a retaining ring at the proximal end and disposed distal of the catheter. An engagement member can be partially disposed in the second lumen and include a distal loop extending through the retaining ring, and a proximal loop extending into the first lumen. Further, an elongated detachment member can slide within the first lumen of the deployment catheter and be disposed through the proximal and distal loops. The detachment member can have a detachment member bump disposed between the proximal and distal loops. Therefore, when the detachment member is disposed within the distal loop and the distal loop is disposed within the retaining ring, the embolic device is in an engaged position, retaining the embolic device proximal to the tip of the catheter. However, when the detachment member is pulled proximally, the detachment member is withdrawn from the distal loop, and the detachment member bump contacts the proximal loop. These acts assist in the disengagement of the distal loop from the retaining ring to thereby release the embolic device. The embolic device can be an embolic coil.

The embolic device deployment system can also have a retainer bump disposed on a proximal end of the engagement member and located outside the second lumen. The retainer bump prevents movement of the engagement member in the distal direction. In one example, this is accomplished because the retainer bump has at least one dimension larger than the second lumen. However, the retainer bump and the detachment member bump are sized to not interfere with each other.

Another example of an embolic device deployment system functions similar to the above, including having an elongated flexible deployment catheter having a first lumen extending therethrough and having proximal and distal ends. However, this example includes an expandable member having a contracted state and an expanded state and having at least two apertures therethrough. The expandable member is disposed in the first lumen and fixed in the first lumen by the expanded state. An engagement member can be partially disposed in at least one aperture, and have a distal loop extending through the retaining ring, and a proximal loop extending into the first lumen. An elongated detachment member can be slidably disposed within the first lumen and another of the apertures. Further, it can be disposed through the proximal and distal loops. The detachment member can also have a detachment member bump disposed on the detachment member between the proximal and distal loops. Similar to the above, when the detachment member is disposed within the distal loop and the distal loop is disposed within the retaining ring, the embolic device is in an engaged position. Then, when the detachment member is pulled proximally, the detachment member is withdrawn from the distal loop, and the detachment member bump contacts the proximal loop to assist in the disengagement of the distal loop from the retaining ring to thereby release the embolic device.

The embolic device deployment system can further include a retainer bump disposed on a proximal end of the engagement member proximal to the aperture. The retainer bump can prevent movement of the engagement member in the distal direction. The retainer bump can also have at least one dimension larger than the aperture. In another example, the retainer bump and the detachment member bump are sized to prevent interference with each other.

A method of deploying an embolic device can includes the steps of disposing an engagement member having distal loop located within a retaining ring of the embolic device. The embolic device can be retained by disposing a distal end of a detachment member in the engagement member distal loop and disposing the detachment member through an engagement member proximal loop. A detachment member bump can be located between the engagement member proximal and distal loops. To deploy, proximally withdraw the detachment member from the engagement member distal loop and contacting the detachment member bump with the engagement member proximal loop, deploying the embolic device. The method can include placing a catheter and the embolic device in a body lumen and moving the catheter and embolic device to a treatment site.

Other examples dispose a retainer bump on the engagement member and restricting distal movement of the engagement member with the retainer bump. In more detail, the engagement member and the detachment member can be disposed in a catheter have a notch formed therein. A portion of the engagement member can be located in the notch and then restricting the movement includes preventing the retainer bump from passing though the notch and engaging the retainer bump and the notch to restrict distal movement.

BRIEF DESCRIPTION OF THE DRAWINGS

This invention is described with particularity in the appended claims. The above and further aspects of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

The drawing figures depict one or more implementations in accord with the present teachings, by way of example only, not by way of limitation. In the figures, like reference numerals refer to the same or similar elements.

FIG. 1 is an enlarged, partially sectional view of an example of an embolic coil delivery system in accordance with the present invention;

FIG. 2 is a cross-section along II-II of FIG. 1;

FIGS. 3A, 3B, and 3C are enlarged, partially sectional views, illustrating releasing the coil in the coil delivery system of FIG. 1;

DETAILED DESCRIPTION

Figure 3C:
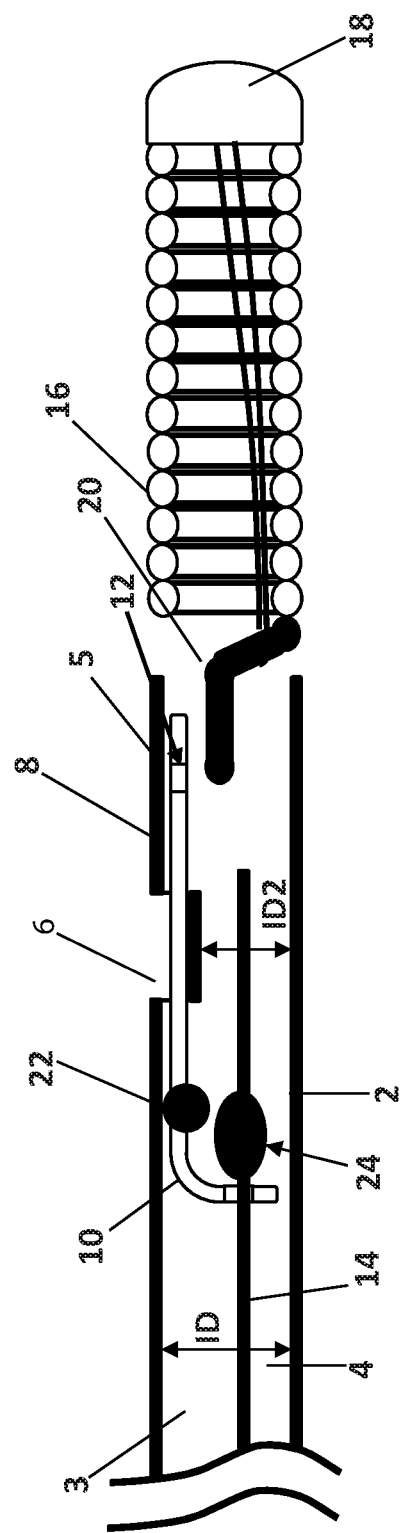

FIG. 1 generally illustrates an example of a vascular occlusive embolic coil delivery system 100 which can include an elongated delivery catheter 2 that may generally comprise a small soft tube and may be a structure of flexible plastic having two ends. The catheter 2 may also comprise a braid or coil reinforced composite construction having an inner layer, a reinforcement layer, and an outer layer. The constructions may include soft polyurethane inner and outer layers that are fused around braided polymer monofilaments. Spiral or coil reinforcement may be used to improve the catheter 2 hoop strength and kink resistance.

The catheter 2 may have a lumen 4 extending from a proximal end 3 to a distal end 5. The catheter 2 may have a first inner diameter ID that forms the lumen 4. The catheter 2 can also include an engagement member notch 6 formed in at least one side of the catheter 2. The engagement member notch 6 can create a reduced inner diameter ID2 as compared to the first inner diameter ID. As shown in FIGS. 1 and 2, an example of the catheter 2 may be a hollow tube like structure and a short inner tube or notch to act as the engagement member notch 6. At its proximal end 3, the catheter 2 may be attached to a surgical device, and at its distal end 5 the catheter may be attached to an embolic device 16 as shown. In one example, the embolic device 16 can eventually release from the distal end 5 to be delivered at a desired location.

The catheter size is selected in consideration of the size, shape, and directionality of the aneurysm or the body lumens the catheter must pass through to get to the treatment site. The catheter 2 may have a total usable length anywhere from 80 centimeters to 165 centimeters and a distal length of anywhere between 5 centimeters to 42 centimeters. The catheter 2 may have an inner diameter ID of anywhere between 0.015 and 0.025 inches. The outer diameter ID may also range in size and may narrow at either its proximal end or distal end. The outer diameter may be 2.7 French or less.

While the distal end 5 of the catheter 2 as shown contains the embolic device 16, the catheter tip may be varied in shape and may curve at an angle.

Also included in the deployment system 100 is an elongated engagement member 8. The engagement member 8 is disposed within the lumen where its ends are constrained at angles. The engagement member 8, in one example, is formed of a small diameter resilient wire, such as nitinol, and includes an engagement member proximal loop 10 and distal loop 12. The engagement member 8 may be a wire device to maintain pushability so it can be manipulated with respect to the catheter 2. In addition, the deployment system 100 may include a retainer bump 22 on the engagement member 8. The retainer bump 22 may vary in shape, size and position in the catheter 2 so it can restrain the movement of the engagement member 8. This restraint, in one example, can be that the retainer bump 22 contacts the notch 6 which stops distal motion of the engagement member 8.

A detachment member 14 can also disposed through the lumen 4 of the catheter 2. The detachment member 14, in one example, may be an elongated retractable fiber that may begin at the proximal end 3 of the catheter 2 and pass through to the distal end 5. The detachment member 14 can pass through the engagement member proximal loop 10 and through the engagement member distal loop 12. The detachment member 14 can serve to interlock the embolic device 16 at the distal end 5 of the catheter 2 until such time as the detachment member 14 is withdrawn proximally. The detachment member 14 can be attached to a surgical device at its proximal end. The detachment member 14 preferably takes the form of a small diameter elongate filament, however, other forms such as wires or tubular structures are also suitable. While the detachment member 14 is preferably formed of nitinol, other metals and materials such as stainless steel, PTFE, nylon, ceramic or glass fiber and composites may also be suitable.

The detachment member 14 can also include a detachment member bump 24 disposed near the distal end of the detachment member 14. As noted in FIG. 1, the detachment member bump 24 can be located between the proximal and distal engagement member loops 10, 12. The detachment member bump 24 can be sized and shaped accordingly so it is larger, and thus cannot pass through, the engagement member loops 10, 12. Note, that in one example, both the retainer bump 22 and the detachment member bump 24 are sized and shaped so as to not interfere with each other.

The deployment system 100 may include an embolic device 16 which, in an example, takes the form of a helically wound embolic coil disposed at the distal end 5 of the catheter 2. While the embolic device 16 as is illustrated is shown as a helically wound coil, other types of embolic devices, such as filaments, braids, foams, expandable meshes and stents, could be delivered using the present deployment system and various other coil configurations could be delivered using this system. A coil may be relatively stiff and made of stainless steel or it may be soft and made of platinum. Extremely soft coils may be made with either a spiral shape or a more complex shape to promote deployment at the desired delivery location and to promote a higher packing density. The diameter of a coil is selected in consideration of the size of the aneurismal sac. Generally, the coil device 16 may be very small and thin, ranging in a variety of shapes and sizes. The coil device 16 may come in various random loop designs to conform to the aneurysm shape, and various deployments of the coil device may be used. A coil can vary in softness and in stiffness. The coil size can range from about twice the width of a human hair to less than one hair's width. The number of loops in a coil may vary. Platinum coils may be between 0.010 inches and 0.025 inches in diameter. A coil may vary from 1 to 60 centimeters in length, with some as long as 100 centimeters. A weld, or solder, bead 18 is formed at the distal end of the embolic device 16 to provide an atraumatic tip for the embolic device 16. The proximal end of the embolic device 16 is attached to the edge of a retaining ring 20. In an example, the retaining ring 20 is coaxial with the proximal end of the embolic device 16.

FIG. 1 illustrates an example of the deployment system 100 when the coil 16 is engaged to the system 100. Approximate to the distal end 5 of the catheter 2, the engagement member 8 is disposed partially within the engagement member notch 6 with the retainer bump 22 proximal of the notch 6. The engagement member proximal loop 10 is proximal to the notch 6 and extends into the lumen 4 of the catheter 2. The engagement member distal loop 12 can also be disposed towards the lumen and extends through the retaining ring 20 of the coil device 16 distal of the engagement member notch 6.

The detachment member 14 extends through the lumen 4 and passes through both the engagement member proximal and distal loops 10, 12. The detachment member bump 24 of the detachment member 14 is disposed between the proximal and distal engagement member loops 10, 12. The interlocking of the detachment member 14 and the engagement member distal loop 12, when the loop 12 is extended through the retaining ring 20, holds the coil 16 in place at the tip of the catheter 2.

FIGS. 1 and 3A illustrate an example of a position of the detachment member 14 to keep the engagement member 8 engaged with the retaining ring 20. The detachment member bump 24 may be shaped and sized to fit into the inner diameter ID2 of the catheter 2 and it can be positioned between the engagement member proximal loop 10 and engagement member distal loop 12 without passing through either. FIG. 1 illustrates the system in this position before the embolic coil 16 is deployed. FIG. 1 shows the position of the detachment member 14 in the lumen 4 of the catheter 2 where the detachment member bump 24 is near the distal end 5 of the lumen 4. The detachment member 14 passes through the engagement member proximal loop 10 and the distal loop 12 where the engagement member 8 is constrained. FIG. 1 also illustrates a position of the engagement member 8 with respect to the detachment member 14. FIG. 2 is a cross section of FIG. 1, illustrating an example that the detachment member 14 and engagement member 8 can be positioned where one is superimposed over the other. The notch 6 separates the detachment member 14 and engagement member 8. FIG. 2 illustrates the placement of the notch 6 creating a second inner diameter ID2 where a portion of the detachment member 14 is positioned as seen in FIG. 1.

FIG. 3A shows the direction of the detachment member 14 as it slides out of the engagement member distal loop 12 to release the coil 16. The detachment member bump 24 is in a proximal position from where it was in FIG. 1. FIG. 3A shows an intermediary position of the detachment member 14 between its initial engagement in FIG. 1 and its proximal movement to begin the disengagement of the coil. The arrow illustrates the direction of movement of the detachment member 14.

As shown in FIG. 3B, the detachment member bump 24 begins to slide toward the proximal end 3 of the catheter 2 until the detachment member bump 24 contacts or is close to contacting the engagement member proximal loop 10. At this point, the detachment member 14 has disengaged from the engagement member distal loop 12 and there is nothing securing the distal loop 12 inside the retaining ring 20. In one example, the distal loop 12 can be manufactured as such to begin removing itself from the retaining ring 20. It can be very soft, pliable, in spring tension, or have shape memory proprieties to assist in the loop's 12 removal from the ring 20.

The detachment member bump 24 may further assist in disengaging the engagement member 8. FIG. 3C illustrates the detachment member 14 after fully withdrawing from the engagement member distal loop 12 and the surgeon continues to move the detachment member 14 proximal of the tip of the catheter 2. The detachment member bump 24 can contact the engagement member proximal loop 10 and, since it cannot pass through the loop 10, proximally displaces the engagement member 8 to assist in the withdrawal of the engagement member distal loop 12 from the retaining ring 20. Once the engagement member 8 fully withdraws from the embolic coil retaining ring 20 as shown in FIG. 3C, the embolic device 16 is released, and the distal end of the engagement member 8 retracts to a position further internal to the delivery catheter 2.

Both FIGS. 3A and 3B demonstrate the direction of movement of the detachment member 14. In an additional example, the detachment member 14 can be limited when moving in the opposite, distal, direction. The engagement member (retainer) bump 22 can prohibit the detachment member 14 from moving too far forward past the tip of the catheter 2 if an additional bump (not illustrated) is placed on the detachment member 14 proximal to the loop 10.

In an example, a Tuohy-Borst type of clamp is attached on the proximal end of the delivery system 100 and serves to prevent movement of the detachment member 14 and the engagement member 8 until the surgeon wishes to deploy the coil 16. In a further example, the detachment member 14 can be removed completely from the catheter 2, taking the engagement member 8 with it. The catheter 2, in an example, can then be used to deploy other surgical tools, however, the ID may be too small. In another example, the catheter 2 can be used to guide a second catheter (not illustrated) over its body after the coil 18 is deployed. In this example, the small ID of the catheter 2 allows it to act as a type of guidewire for a larger catheter.

Figure 4:
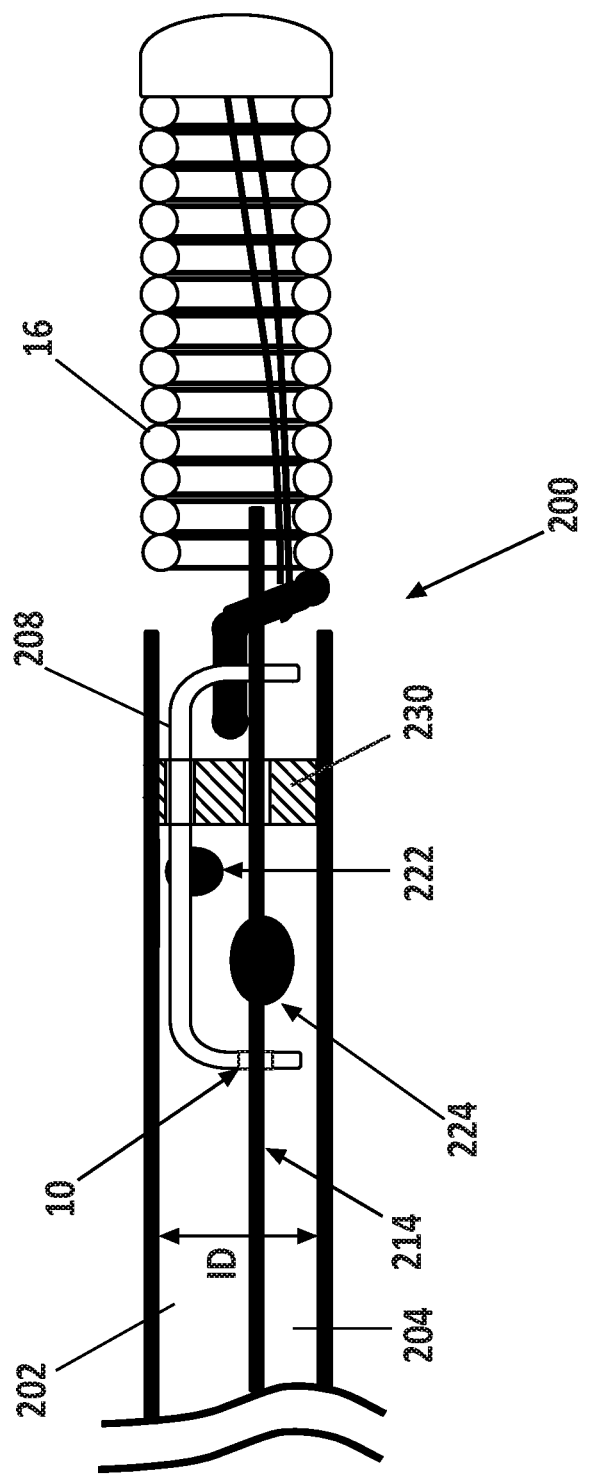
FIG. 4 is an enlarged, partially sectional view of another example of a coil delivery system.

In FIG. 4, another example of an embolic coil delivery system 200 is illustrated. The system 200 functions similarly to the system 100 described above but can adapt to any generic catheter 202. In the previous example, the catheter 2 has a notch 6, to retain the engagement member 8. The system 200 can have an expandable member 230 disposed along a detachment member 214 and an engagement member 208. Here, the entire system 200 can be disposed within the catheter 202 and the expandable member 230 is in its minimized configuration. Here, the expandable member 230 is as small or smaller as the inner diameter ID of the catheter 202. Once placed within the lumen 204, the expandable member 230 can be expanded to contact the catheter 202 and be fixed in place. Both the engagement member 208 and the detachment member 214 can pass through the expandable member 230 but their respective bumps 222, 224 can be constrained as in the example above to prevent over extension of the engagement member 208 and allow the detachment member 214 to assist in the disengagement of the coil 16. The expandable member 230 can be inflatable, expandable, or spring loaded as is known in the art. Further, the expandable member 230 can be a fixed size and adhered to the catheter 202 using known adhesives.

Figure 5:
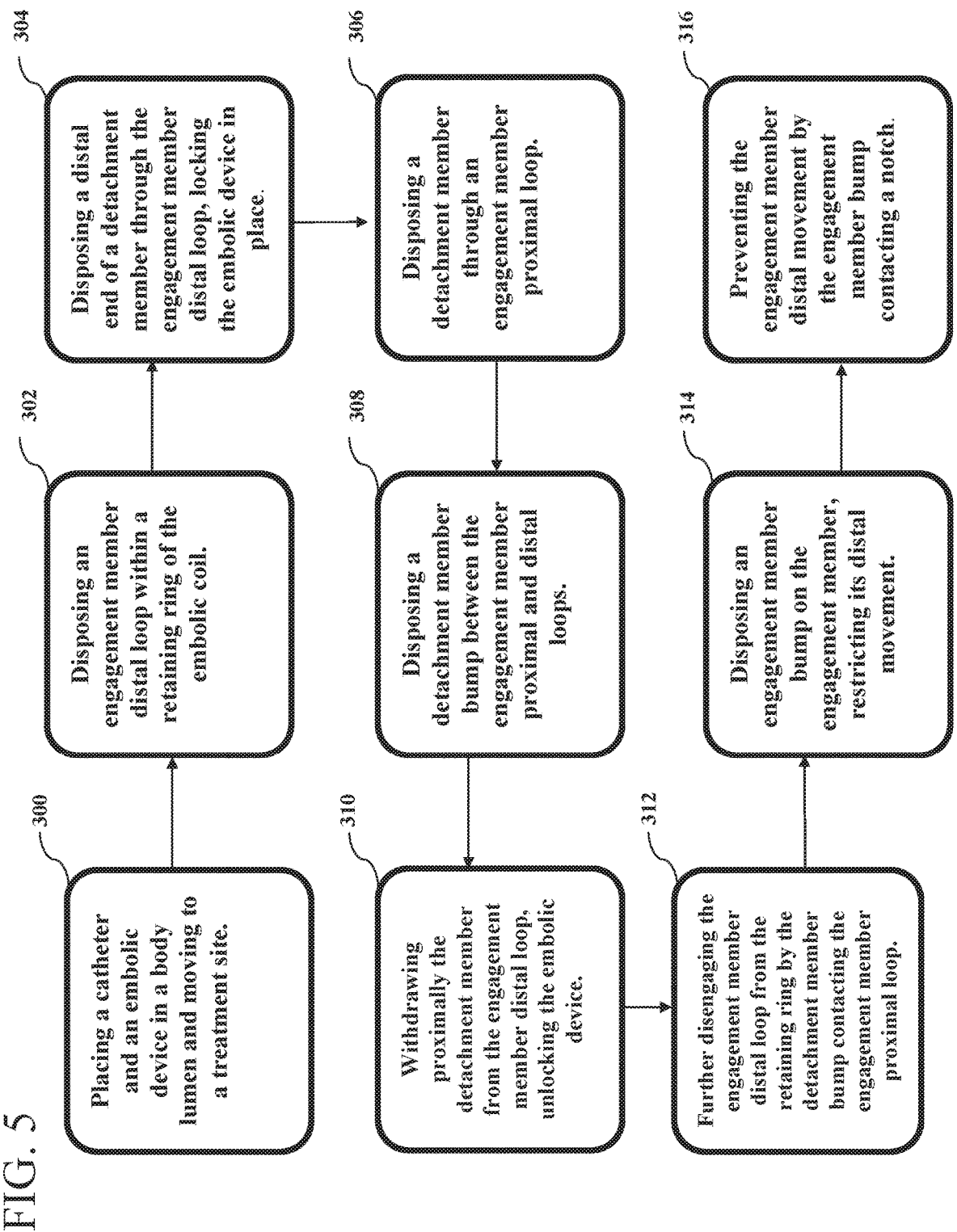
FIG. 5 is a flow chart of the method of delivering a coil of the present invention.

FIG. 5 illustrates a method of deploying a coil 16 of the present invention. An example of a method includes placing a catheter 2 and an embolic device 16 in a body lumen 4 and moving it to a treatment site (step 300). An engagement member distal loop 12 can be disposed within a retaining ring 20 of the embolic coil 16 (step 302). Further, a distal end of a detachment member 14 can be disposed through the engagement member distal loop 12, locking the embolic device 16 in place (step 304). The detachment member 14 can also be disposed through an engagement member proximal loop 10 (step 306). A detachment member bump 24 can be disposed between the engagement member proximal and distal loops 10, 12 (step 308). The detachment member 14 can be proximally withdrawn from the engagement member distal loop 12, disengaging the embolic device 16 (step 310). Further, the detachment member bump 24 can contact the engagement member proximal loop 10 so as to further disengage the engagement member distal loop 12 from the retaining ring 20 (step 312). Additionally, an engagement member enlarged, partially sectional enlarged, partially sectional (retainer) bump 22 can be disposed on the engagement member 8 restricting its distal movement (step 314). The engagement member bump 22 can contact a notch 6 in the catheter 2 to prevent distal movement of the engagement member 8 (step 316).

As is apparent, there are numerous modifications of the preferred example described above which will be readily apparent to one skilled in the art, such as many variations and modifications of the embolic device including numerous coil winding configurations, or alternatively other types of embolic devices. Also, there are many possible variations in the materials and configurations of the release mechanism. These modifications would be apparent to those having ordinary skill in the art to which this invention relates and are intended to be within the scope of the claims which follow.

What is claimed is:

1. An embolic implantation system comprising:
   an elongated delivery tube configured to traverse vasculature and comprising a lumen therethrough;
   an embolic implantable device comprising a retaining ring;
   a flexible loop engaged to the elongated delivery tube and extending through the retaining ring;
   an elongated detachment member being slidably disposed within the lumen of the delivery tube and the flexible loop so that the embolic implantable device is thereby engaged to the delivery tube and the elongated detachment member is slidable in a proximal direction to exit the flexible loop so that the flexible loop can exit the retaining ring, the elongated detachment member comprising a distal bump extending therefrom;
   a distal obstruction positioned approximate a distal end of the delivery tube and shaped to engage the distal bump to obstruct distal movement of the distal bump when the distal obstruction is engaged to the distal bump;
   wherein the distal obstruction comprises the flexible loop and the retaining ring when the embolic implantable device is engaged to the delivery tube; and
   an engagement member comprising the flexible loop and a proximal loop positioned within the lumen of the delivery tube approximate the distal end of the delivery tube,
      wherein the elongated detachment member further comprises a proximal bump shaped to engage the proximal loop upon proximal movement of the proximal bump into the proximal loop.

2. The embolic implantation system of claim 1, wherein the flexible loop and the proximal loop are affixed within the lumen of the delivery tube.

3. The embolic implantation system of claim 1, wherein the engagement member is slidable, and thereby the flexible loop and proximal loop are each slidable, in the proximal direction upon proximal movement of the proximal bump when the proximal bump is engaged to the proximal loop.

4. The embolic implantation system of claim 3, further comprising:
   an engagement member holder affixed in relation to the elongated delivery tube through which a portion of the engagement member is slidably disposed,
      wherein the engagement member comprises a retainer bump thereon positioned in a proximal direction in relation to the engagement member holder and sized to engage the engagement member holder to inhibit distal movement of the engagement member through the engagement member holder.

5. The embolic implantation system of claim 3, wherein the engagement member is configured to slide in a proximal direction, upon proximal movement of the proximal bump when the proximal bump is engaged to the proximal loop, to cause the flexible loop to exit the retaining ring.

6. An embolic implantation system, comprising:
   an elongated delivery tube configured to traverse vasculature and comprising a lumen therethrough;
   a pull wire slidably disposed in the lumen and comprising a distal bump affixed on a distal portion of the pull wire;
   an embolic implant comprising an opening;
   a flexible loop engaged to the elongated delivery tube, extending through the opening of the embolic implant, and a looped around the pull wire so that the embolic implant is detachably attached to the elongated delivery tube and the distal bump on the pull wire is obstructed from sliding distally through the flexible loop; and
   an engagement member comprising the flexible loop and a proximal obstruction positioned within the lumen of the delivery tube approximate a distal end of the delivery tube,
      wherein the pull wire further comprises a proximal bump shaped to engage the proximal obstruction upon proximal movement of the proximal bump into the proximal obstruction.

7. The embolic implantation system of claim 6, wherein the flexible loop and the proximal obstruction are affixed within the lumen of the delivery tube.

8. The embolic implantation system of claim 6, wherein the engagement member is slidable, and thereby the flexible loop and proximal obstruction are each slidable, in a proximal direction upon proximal movement of the proximal bump when the proximal bump is engaged to the proximal obstruction.

9. The embolic implantation system of claim 8, further comprising:
   an engagement member lumen affixed in relation to the elongated delivery tube and through which a portion of the engagement member is slidably disposed,
      wherein the engagement member comprises a retainer bump thereon positioned in a proximal direction in relation to the engagement member lumen and sized to inhibit distal movement of the engagement member through the engagement member lumen.

10. The embolic implantation system of claim 8, wherein the engagement member is configured to slide in a proximal direction, upon proximal movement of the proximal bump when the proximal bump is engaged to the proximal obstruction, to cause the flexible loop to exit the opening of the embolic implant.

11. A method comprising:
engaging a flexible loop to an elongated delivery tube;
extending the flexible loop through a retaining ring of an embolic implant;
positioning a distal bump extending from a pull wire and near a distal end of the pull wire;
extending a pull wire through a lumen of the delivery tube and an opening of the flexible loop to thereby engage the embolic implant to the delivery tube;
positioning an obstruction in a distal direction in relation to the distal bump which obstructs distal movement of the pull wire when the distal bump is pushed distally against the obstruction;
positioning the pull wire so that it is slidable through the delivery tube in a proximal direction to exit the opening of the flexible loop;
positioning the flexible loop and the retaining ring to form the obstruction so that the flexible loop and retaining ring obstructs distal movement of the pull wire when the distal bump is pushed against the flexible loop and/or the retaining ring; and
positioning a proximal bump extending from the pull wire and in the proximal direction in relation to the distal bump, and
positioning a proximal aperture within the delivery tube and in the distal direction in relation to the proximal bump, the proximal aperture being sized to inhibit the proximal bump from passing therethrough.

12. The method of claim 11, further comprising: affixing the proximal aperture and flexible loop to the delivery tube.

13. The method of claim 11, further comprising: joining the flexible loop and the proximal aperture to a slidable engagement member so that the flexible loop and proximal aperture are collectively slidable in the proximal direction upon proximal movement of the proximal bump against the proximal aperture.

14. The method of claim 13, further comprising:
affixing a retainer bump on the engagement member; and
disposing a portion of the engagement member through a notch sized such that the retainer bump is inhibited from passing therethrough and the retainer bump is positioned in a proximal direction in relation to the notch.

15. The method of claim 13, further comprising:
sliding the engagement member in the proximal direction, upon proximal movement of the proximal bump against the proximal aperture to cause the flexible loop to exit the retaining ring.

* * * * *